United States Patent
Bernston et al.

(10) Patent No.: US 8,027,848 B2
(45) Date of Patent: Sep. 27, 2011

(54) CONTEXT MANAGING MOBILE COMPUTING FRAMEWORK FOR ENTERPRISE APPLICATION

(75) Inventors: Glenn M. Bernston, Beverly, MA (US); Chao Young Lee, Weston, MA (US); George A. Madrid, Arlington, MA (US); Maulin P. Shah, Houston, TX (US); Sanjay S. Vakil, Arlington, MA (US)

(73) Assignee: Patient Keeper, Inc, Waltham, MA (US)

( * ) Notice: Subject to any disclaimer, the term of this patent is extended or adjusted under 35 U.S.C. 154(b) by 2065 days.

(21) Appl. No.: 10/335,545

(22) Filed: Dec. 31, 2002

(65) Prior Publication Data

US 2003/0158753 A1    Aug. 21, 2003

Related U.S. Application Data

(63) Continuation-in-part of application No. 10/238,841, filed on Sep. 9, 2002, now abandoned, which is a continuation of application No. 10/118,592, filed on Apr. 8, 2002, now abandoned.

(60) Provisional application No. 60/282,249, filed on Apr. 6, 2001, provisional application No. 60/282,131, filed on Apr. 6, 2001.

(51) Int. Cl.
*G06Q 10/00* (2006.01)
*G06Q 50/00* (2006.01)
*G06Q 40/00* (2006.01)

(52) U.S. Cl. .................... 705/2; 705/3; 705/4

(58) Field of Classification Search .......... 705/2–4
See application file for complete search history.

(56) References Cited

U.S. PATENT DOCUMENTS

| | | | | |
|---|---|---|---|---|
| 5,335,664 A | * | 8/1994 | Nagashima | 600/508 |
| 5,359,509 A | * | 10/1994 | Little et al. | 705/2 |
| 5,392,390 A | | 2/1995 | Crozier | |
| 5,429,119 A | * | 7/1995 | Griffin et al. | 600/200 |
| 5,538,007 A | * | 7/1996 | Gorman | 600/523 |
| 5,557,514 A | * | 9/1996 | Seare et al. | 705/2 |
| 5,664,109 A | * | 9/1997 | Johnson et al. | 705/2 |
| 5,704,044 A | * | 12/1997 | Tarter et al. | 705/4 |
| 5,748,365 A | * | 5/1998 | Chen | 359/366 |
| 5,749,365 A | * | 5/1998 | Magill | 600/484 |
| 5,781,442 A | * | 7/1998 | Engleson et al. | 700/214 |
| 5,819,228 A | * | 10/1998 | Spiro | 705/2 |
| 5,832,447 A | * | 11/1998 | Rieker et al. | 705/2 |
| 5,835,897 A | * | 11/1998 | Dang | 705/2 |
| 5,857,201 A | | 1/1999 | Wright, Jr. et al. | |
| 6,000,000 A | | 12/1999 | Hawkins et al. | |
| 6,057,758 A | * | 5/2000 | Dempsey et al. | 340/539.12 |

(Continued)

OTHER PUBLICATIONS

Context Management ("CCOW") Specification, Component Technology Mapping: ActiveX, Version CM-1.2, Health Level Seven, Jun. 2000, pp. 1-48.

(Continued)

*Primary Examiner* — Jason B Dunham
*Assistant Examiner* — Amber Altschul
(74) *Attorney, Agent, or Firm* — Brient Intellectual Property Law, LLC

(57) ABSTRACT

A framework for handheld computing devices comprises a user interface controlling the display, selection and launching of program modules, controls patient context within the program modules, and provides for messaging and sharing of databases between and among program modules. Databases are shared between the program modules by the publishing of XML and metadata identifying the structure of the databases.

6 Claims, 4 Drawing Sheets

U.S. PATENT DOCUMENTS 6,167,412 A * 12/2000 Simons ................... 708/105
7,110,955 B1 * 9/2006 Barhnart et al. ............. 705/3

OTHER PUBLICATIONS

Context Management ("CCOW") Specification, Technology- and Subject-Independent Component Architecture, Version CM-1.2, Health Level Seven, Jun. 2000, pp. 1-228.

Context Management ("CCOW") Specification, Subject Data Definitions, Version CM-1.2, Health Level Seven, Jun. 2000, pp. 1-32.

Context Management ("CCOW") Specification, Component Technology Mapping: Web, Version CM-1.2, Health Level Seven, Jun. 2000, pp. 1-79.

Context Management ("CCOW") Specification, User Interface: Microsoft Windows and Web Browsers, Version CM-1.2, Health Level Seven, Jun. 2000, pp. 1-17.

* cited by examiner

```
20

21
                          )
<Store storied+"data">
      <Field frame= "pID" type="U"/>—23
      <Field frame= "foo" type="C"/>—25
</Store>                  )
                         27
```

70 ⤴

71
)
```
<Store storied+"data">
      <Field fname="foo"  type="C"/>
            sname="foobar"/>
</Store>                      )
                              73
```

FIG. 4

CONTEXT MANAGING MOBILE COMPUTING FRAMEWORK FOR ENTERPRISE APPLICATION

RELATED APPLICATION(S)

This application is a continuation-in-part of U.S. application Ser. No. 10/238,841, filed Sep. 9, 2002 now abandoned, which was a continuation of U.S. application Ser. No. 10/118,592, filed Apr. 8, 2002 now abandoned, which claims the benefit of U.S. Provisional Application No. 60/282,249, filed on Apr. 6, 2001 and to U.S. Provisional Application No. 60/282,131, filed on Apr. 6, 2001.

The entire teachings of the above applications are incorporated herein by reference.

BACKGROUND OF THE INVENTION

This application relates generally to handheld computer devices and more specifically to a framework for handheld computer devices used in the health care industry.

In the health care industry, health care providers have become increasingly dependent on the use of computer systems and software to keep track of all aspects of patient data, including clinical, administrative and billing information. In the mid-1990's, CCOW (Clinical Context Object Workgroup) was developed to help aid health care providers manage patient data. The CCOW standard, now the ANSI approved Health Level 7 Context Management Standard version 1.4, establishes the basis for ensuring secure and consistent access to patient information from heterogeneous sources through synchronizing and coordinating applications—such as those used for patient registration, order entry and results reporting—so that they instinctively follow a specific context, including the identity of a user, a patient or a specific clinical observation. CCOW-compliant applications coordinate with each other via a behind-the-scenes context manager that enables them to work together in ways that behave like a single system from the health care provider's perspective.

In more recent years, health care providers have begun to use handheld computing devices and software, such as that offered by PatientKeeper, Inc., to keep track of patient data. The PatientKeeper systems are described in U.S. patent application Ser. No. 09/356,543, titled "Device for Automating Billing Reimbursement," by inventors Matthew D. Barnhart, Stephen S. Hau, Yuri Ostrovsky and MinPont Chien, filed on Jul. 19, 1999 and U.S. patent application Ser. No. 09/356,751, titled "System for Automating Billing Reimbursement," by inventors Matthew D. Barnhart, Stephen S. Hau, Patrick McCormick, George A. Madrid, Craig A. Fields and Sanjay S. Vakil, filed on Jul. 19, 1999, the teachings of which are incorporated herein by reference.

In a typical health care environment, a hospital, for example, doctors will carry a handheld device with them as they treat patients. As tests are performed, diagnoses made, and treatment administered, a doctor can note all of the activity in the handheld device. After seeing several patients, the doctor then synchronizes the handheld device with a server which is connected to the hospital's main computer network. All patient data collected in the handheld is then uploaded to the hospital's main information system and at the same time, any patient data in the main system which has been updated since the last synchronization can be downloaded to the handheld device.

SUMMARY OF THE INVENTION

To perform the tasks of tracking clinical data, lab tests, billing data, and administrative data, etc., the handheld device must be capable of running programs for all of these applications. Furthermore, to ensure that changes to patient records made in one application transfer to the other applications on the handheld device, there must be a way for the application programs to communicated and share data specific to each patient. Thus, it is desirable to have a CCOW-like program on a handheld device which can manage the context of each application program.

The problem is that CCOW is written for devices with the computing power of a common desktop computer, not a handheld device, which typically has considerably less computing power and memory than desktop computers. Furthermore, a handheld device which is carried around by a doctor while treating patients need not have the full capabilities of a network computer system running CCOW. Thus, it is desirable to have an application which can run on a handheld device and manage the context of data being used by a plurality of application program modules.

The present invention comprises a framework for handheld devices which provides CCOW-like context management of data and program modules. The framework provides a user interface which presents all available program modules to the user as if they were a single application and allows for navigation between program modules. The framework also has a patient manager which allows a patient to be selected from a list and that patient's data to be recalled from memory. As a healthcare provider switches between program modules on the handheld device, the framework launches the subsequent program module in the same context as the previous program module, i.e. data for the current patient is immediately available and displayed in the subsequent program module. The framework also provides for inter-module integration which allows program modules to use other program modules on the handheld to retrieve and process data and allows messages to be sent between the program modules. Program modules are created with meta-data representations of the databases used by the applications. By communicating this meta-data to the server during synchronization, data can be retrieved from the server in a single pass (Turnkey Synchronization). Centralized Administration of the program modules, their data and the handheld framework is also provided.

A handheld device for providing access to patient medical data and software has a display, a plurality of program applications which process medical data, and a framework program which controls selection of the program applications, controls the patient context of each application, and controls the sharing of data between the applications. The framework may have metadata descriptions of how data is stored on the handheld device. The framework may control the synchronization of the handheld device to a server, and this synchronization may be effected in a single transaction. The handheld device may further comprise a library of databases and a messaging conduit for communicating messages between program modules. The handheld device may also comprise a user interface for displaying a particular program module, one or more tabs displaying and allowing the selection of other available program modules, and a patient selector.

A method for integrating health care applications on a handheld device comprises the steps of providing a handheld device having memory and a plurality of program modules stored in the memory, providing a framework program having libraries of data and a messaging conduit, selecting a first program module and a particular patient, from within the first program module, requesting data from a second program module, opening the second program module maintaining the context of the selected patient, providing the requested data for the patient, and returning to the first program module.

A method for communicating between program modules on a handheld device comprises the steps of providing a handheld device having memory and a plurality of program modules stored in the memory, providing a framework program having libraries of data and a messaging conduit, in a first program module, requesting data from a second program module by sending the data request through the messaging conduit to the framework, activating the second program module and checking if there are messages, conveying the data request from the framework to the second program module, processing the data in the second program module and returning it to the framework which then returns it to the first program module.

A user interface for operating health care applications on a handheld device comprises a window displaying a user interface of an active program module, a tab bar with tabs for selecting each available program module on the handheld device, and a patient selector for controlling the patient context of the program modules.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 4 shows an example of metadata for a server application.

DETAILED DESCRIPTION OF THE INVENTION

A description of preferred embodiments of the invention follows.

While the following description mainly pertains to use of the present invention in the health care industry, much of the methods and software described herein are broad enough for general application to a variety of fields.

The present invention is a framework for a handheld device. This handheld framework serves to integrate a plurality of program modules on the handheld device. Each program module administers its own database, but publishes the necessary information needed by the handheld framework to access those portions of the database which it is intended to access. Similarly, program modules can use this information to access data from other program modules' databases. The framework provides a User Interface, an Application Programming Interface, Metadata XML data description, Module Integration (messaging between modules), Centralized Administration and Turnkey Synchronization. The framework is platform independent and can utilize single (Palm) or multiple (Windows CE) threaded operating systems.

User Interface

Figures 1, 2:
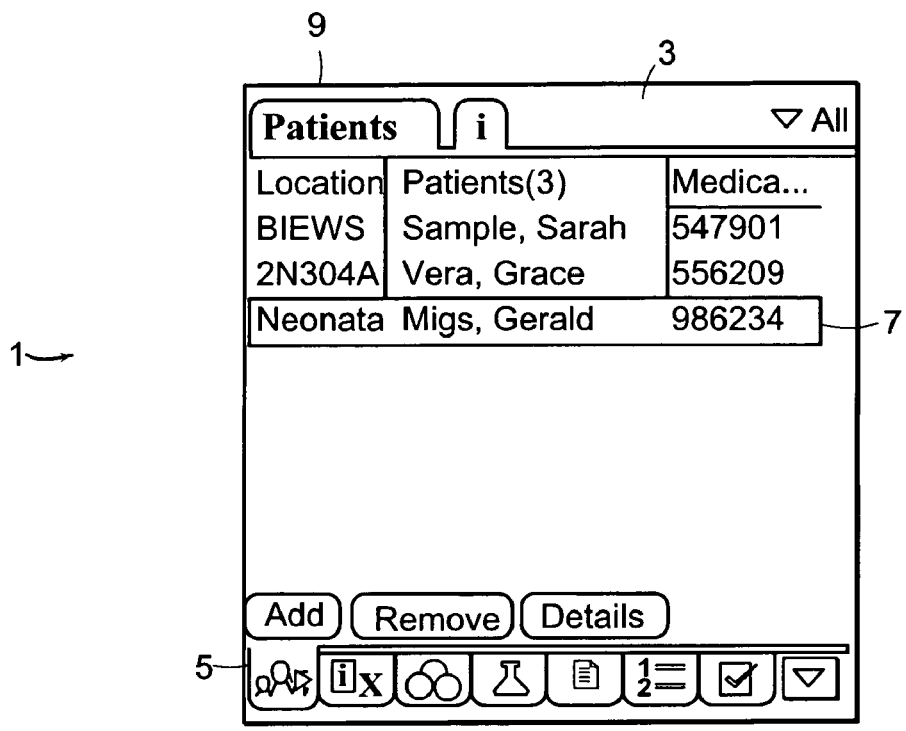
FIG. 1 shows a handheld device displaying the User Interface.
FIG. 2 is an example of metadata.

The first feature of the handheld framework that a user will notice is the User Interface. FIG. 1 shows a handheld device 1 displaying the User Interface 3. At the bottom of the screen is a tab bar 5. The tab bar contains an icon for each of the available program modules on the handheld device. As program modules are added to the handheld device, their icons are added to the tab bar. The user can select a program module by tapping on the desired module's tab. The program modules can be provided with the handheld framework or developed by third party developers as well.

In the middle of the screen is the main application space 7. The active program module is displayed in the application space 7. When a user selects a different program module by tapping on its tab, the newly selected program module is launched in the application space 7. The application space 7 may also have a scroll bar if one is needed to display information that cannot fit in a single screen. The User Interface also has a drop down Patient List 9. This list of patients allows the user to select any of the patients whose data currently resides on the handheld device. Doctors can select which patients they intend to attend to on a given rotation (or it can be done automatically for them) and then download those patients into the handheld device. The doctor then only need select from the Patient List 9 as he moves from one patient to the next. The Patient List is common across all of the program modules and selecting a particular patient in one program module will result in all of the other program modules changing to that patient's context as well. This synchronization of all the program modules to the same patient happens automatically when a doctor selects a patient from the Patient List.

A goal of the User Interface 3 is to present all of the available program modules to a user as if they were all one application. Thus, whether a doctor is using program modules provided with the handheld framework or program modules written by a third party, they will all look like a single application. The User Interface is also platform independent, meaning it will appear and function the same on the various handheld device operating systems, such as the Palm OS or Pocket PC/Windows CE platform. This facilitates more efficient programming for third-party developers writing their own custom program modules. The handheld framework provides rules for writing custom program modules such that they will automatically interoperate with the handheld framework and other program modules on the handheld device.

Application Programming Interface

The Application Programming Interface (API) is a set of functions for use by any developer wishing to create an application to run with the handheld framework. These functions remove much of the overhead work otherwise borne by software developers. With work already done for such difficult matters as memory and database management, the technical knowledge needed by the developer is reduced, whether it be a third-party developer or an employee of the provider of the handheld framework. Furthermore, a program module written according to the API will have operational consistency, exchangeability of data with other program modules also running on the handheld framework, and context management. The API has libraries of functions available to a programmer as well as the necessary documentation describing the way data is stored in a handheld device running the handheld framework.

Included in the API is a methodology for describing data. The method sets forth how data is described in the databases residing on the handheld device as well as on a server. The preferred method for describing data is using industry-standard extensible markup language, or XML. XML is used to put the data in an efficient format. This assists programmers in specifying how data is shared between program modules on the handheld device as well as how data is transferred between the handheld device and the server during synchronization operations. The use of XML also reduces the actual amount of data which needs to be transferred.

An application programmer uses the XML standards of the handheld framework when developing their own proprietary program modules. The programmer selects which data entities a program module will use and then creates the program module using the necessary XML descriptions of the data. The handheld framework will then be able to fully communicate with the databases which accompany the program module and any transfer of data to or from the program module to the handheld framework, server, or other program module will be transparent to the user.

Rules for Describing Data

The handheld framework provides the rules necessary for describing data. Since it is preferred that each program module owns its own databases, how the data is described in those databases must be shared with the handheld framework and other program modules with which data is to be shared. This is accomplished with a metadata description of all the data needed by a program module on the handheld device. In the preferred embodiment, the metadata is described in XML.

A developer writing a program module to work with the handheld framework must create a Data Store according to the rules provided with the handheld framework. The Data Store is separate from the main software code and describes the tables of data that the program module may use as well as the XML metadata describing how the data is stored. By allowing the handheld framework to see the metadata, the handheld framework, server or other program modules will know how to interact with the program module and exchange data with it. The Data Store metadata is used in the same way on any platform.

An example of metadata is shown in FIG. 2. The metadata 20 may have a value 21, a definition of an integer field 23 and a definition of a character field 25. In this example, the metadata is defining the fields "pID" and "foo" for a particular record. If the code for a particular program module asks for "foo," the handheld framework looks to the metadata to see how to obtain "foo." The metadata instructs the handheld framework as to where "foo" can be located. The handheld framework then retrieves the data and returns it to the program module requesting it. This method is used for communication between the handheld framework and program modules, between one program module and another, and between the handheld device and a server. The handheld framework also provides for methods of packaging, sending, receiving and unpacking data. The use of the metadata in packaging data allows for efficient compression and transmission of the data.

Module Integration in Single or Multiple threaded Operating Systems

Module integration allows any program module to access any open feature in any other program module on the handheld device. For example, a module that knows about a drug reference can provide a service to other modules that need to know about drugs, i.e. a prescription module wants to know about hazardous drug-drug interactions. Any program module can publish any features or functionality that it wants to provide as a service to other modules. For example, a Diagnosis module may wish to run inside a Charge/Billing module since billing charges must be associated with a diagnosis. In general, messages are sent between program modules to request data, services or alter context.

Figure 5:
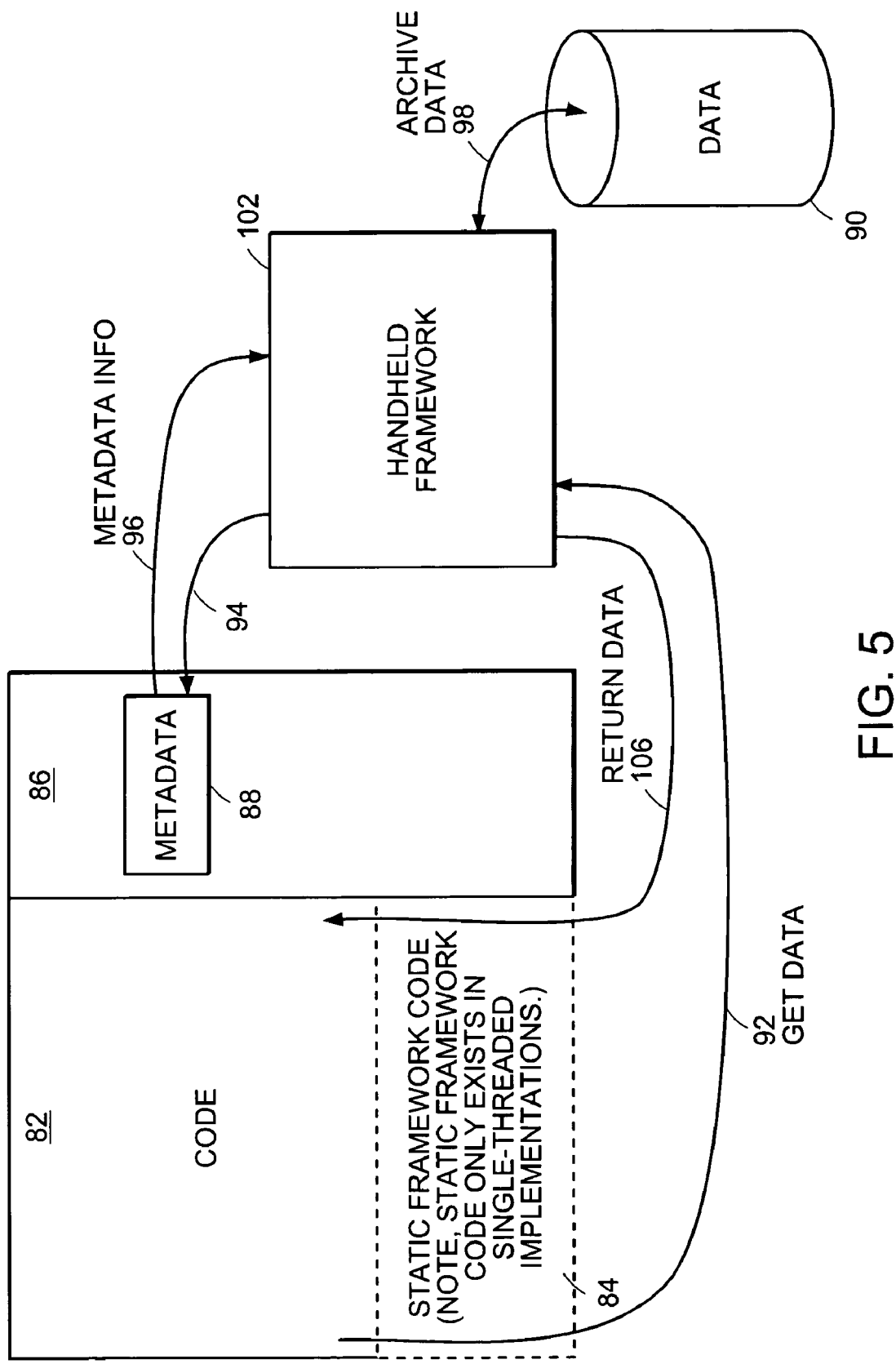
FIG. 5 shows a diagrammatic representation of how a program module retrieves data by way of the handheld framework.

FIG. 5 shows a diagram representation 80 of how the software code 82 of a particular program module interacts with the handheld framework 102 to retrieve data from a database 90. The diagram 80 is composed of the main program code 82, handheld framework 102, and a data store 86, which is comprised of the metadata table description and data 88. The data store may also comprise a schema describing how all of the codes and tables fit together. The diagram 80 shows the process by which a data object is retrieved at the request of the software code 82.

When the code 82 requires data from a particular database, it sends a request 92 to get data to the handheld framework 102. In a single threaded OS, a portion of the framework's code is statically linked into the software code to enable it to communicate with the handheld framework 102. The handheld framework 102 then checks at 94 with the metadata tables 88 how the data is stored. At 96, the metadata tables 88 inform the handheld framework 102 how the data is stored by revealing the metadata information as shown in FIG. 2. The handheld framework 102 then retrieves the data at 98 from the database 90. Finally, the handheld framework 102 returns the data at 100 to the program module's main code 82.

Handheld devices currently come with either single or multiple threaded operating systems. This refers to the number of applications that can run on the handheld device at a given time. The Pocket PC/Windows CE platform is an example of a multiple threaded operating system. The Palm OS platform is currently single threaded, but will likely move to multiple threaded in the near future. Multiple threaded environments provide the advantage of being able to execute certain functions in multiple program modules at the same time. For example, a message regarding laboratory test results can be sent to both a Diagnosis module and a Billing module at the same time.

When one program module is active and displayed in the application space and the user then selects another program module via the tab bar, the newly selected program module is then displayed in the application space. In a multiple threaded environment, the first program module can actually remain open while the second program module is being used. However, in a single threaded environment, the first application is closed and then the second application opened. Nevertheless, the handheld framework provides for the closing of the first and opening of the second program modules such that the transition is transparent to the user. Thus, one can see that it is easier for program modules to communicate with each other in a multiple threaded environment where they can both run simultaneously, than in a single threaded environment where only one program module is active at a given time. The handheld framework provides a solution to this problem by executing a message transfer sequence whereby messages between program modules travel through the handheld framework, thus simulating a multiple threaded environment on a single threaded handheld device.

Figure 3:
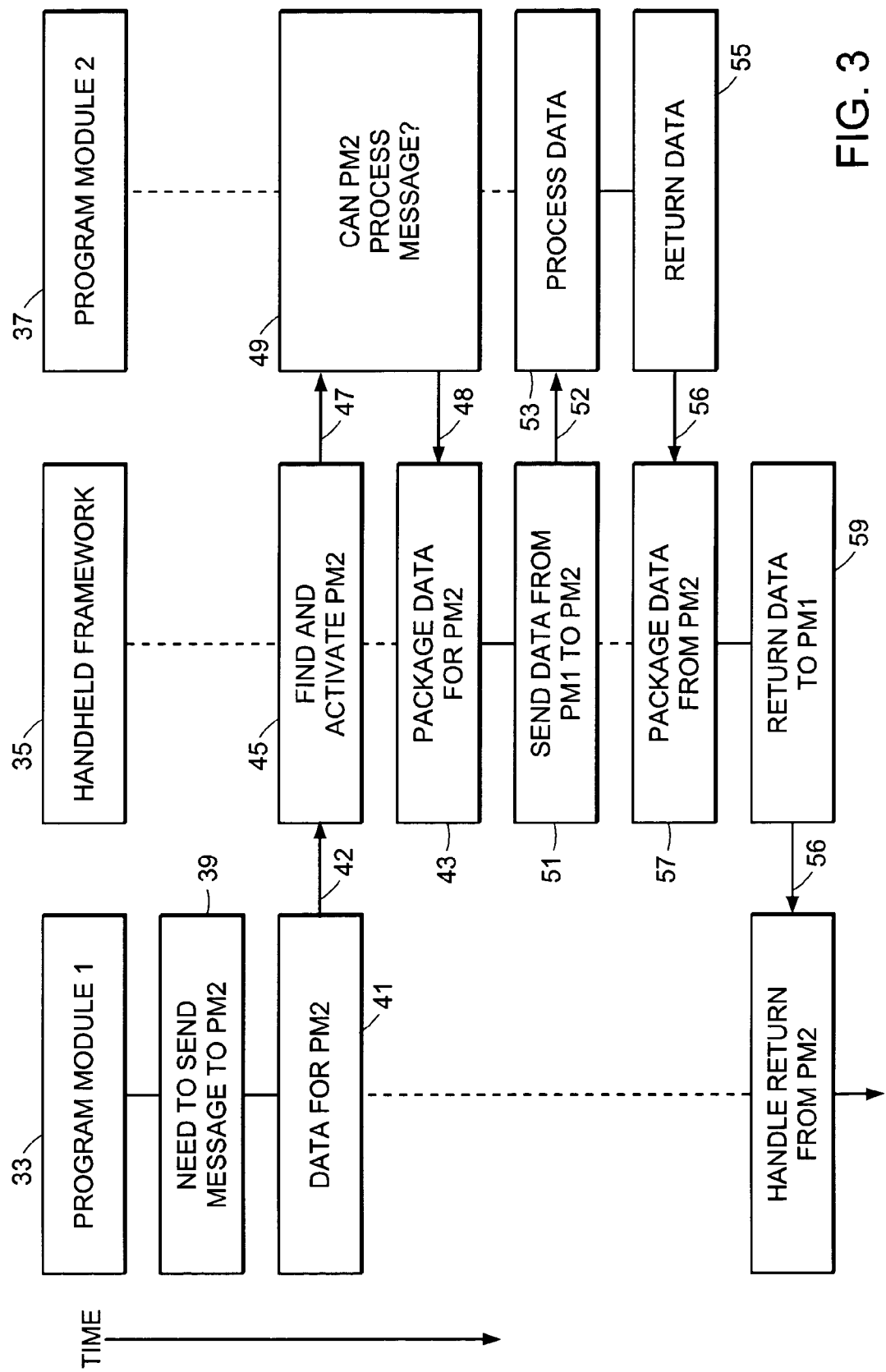
FIG. 3 shows an example of a sequence for sub-launching a second program module.

FIG. 3 shows an example of a sequence for handling messaging (on Palm OS devices, this is accomplished via a sub-launch mechanism). Dotted lines are shown where the program module or handheld framework are not active in a single threaded environment, but are active in a multiple threaded environment. In this example, Program Module 1 (PM1) 33 requires the help of Program Module 2 (PM2) 37 to process some data in a way that only PM2 can do. Thus, PM1 first determines at 39 that it must send a message to PM2 37. PM1 then prepares at 41 the data for PM2 and sends it at 42 to the Handheld Framework 35. The Handheld Framework then packages the data at 43 for PM2 using the published metadata of PM2 to know how PM2 expects to receive data. The Handheld Framework 35 then finds PM2 at 45 and activates it at 47. The first action PM2 takes is to inquire at 49 whether or not there are any messages waiting for it on the Handheld Framework 35. The Handheld Framework 35 then sends the data at 52 and message at 51 from PM1 to PM2. PM2 then processes the data at 53 and returns it at 55 to the Handheld Framework 35. The Handheld Framework 35 then packages the data at 57 for PM1 and returns it to PM1 at 59. The result is that PM1 is able to have data processed by the code of PM2 and returned to it in the format designated by its metadata. This process works mostly the same way for a multiple threaded environment. The main difference would be that the step 45 of finding PM2 could involve searching for an open application.

Turnkey Synchronization

Communication between the program modules on the handheld device and the server works very similarly to communication between program modules and other program modules. Essentially, the server publishes metadata teaching the types of fields available on the server and the handheld framework provides for a proper mapping of those fields to the corresponding fields in the program modules on the handheld device.

FIG. 4 shows an example of metadata for a server application. This metadata 70 is similar to that of the metadata 20 in FIG. 2. However, in addition to the definition of an "fname" 71 for a field in the handheld framework, there is a corresponding "sname" 73 referring to the equivalent field on the server. Thus, in this example, whereas the handheld framework would refer to this field as "foo," the server would refer to it as "foobar."

This effective mapping of fields on the handheld framework to the fields on the server allows for efficient packaging of data and requests for data. As a result, all data requests and fulfillments of those requests can occur rapidly in a single transaction between the handheld device and the server. This is referred to as Turnkey Synchronization.

Centralized Administration

Synchronization with the server also allows for centralized administration of a plurality of handheld devices at the server end. Management of all levels of the handheld devices is possible. For example, individual program modules can be automatically updated, new program modules can be added, and old program modules can be deleted. The handheld framework itself could also be updated using this process.

While this invention has been particularly shown and described with references to preferred embodiments thereof, it will be understood by those skilled in the art that various changes in form and details may be made therein without departing from the scope of the invention encompassed by the appended claims.

What is claimed is:

1. A handheld device providing a patient medical data interface comprising:
   a display, memory, and at least one processor;
   a plurality of application programs, each processing medical data; and
   a framework program that controls selection of the application programs to present user interfaces on the display, controls patient context of each application program, and controls sharing of data between the application programs,
   wherein first data is displayed for a given patient in a first application program and upon switching from the first application program to a second application program, the framework displays the second application program and displays second data for said given patient in the second application program.

2. The handheld device of claim 1 wherein the framework program comprises metadata descriptions of how data is stored for each application program.

3. The handheld device of claim 1 wherein the framework program controls the synchronization of data between the handheld device and a server.

4. The handheld device of claim 3 wherein the synchronization is effected in a single transaction wherein the framework program communicates to the server the type of data it requires and the server supplies the requested data.

5. The handheld device of claim 1 further comprising a library of databases and a messaging conduit accepting messages from the application programs and delivering messages to the application programs.

6. The handheld device of claim 1 further comprising a user interface displaying a selected application program, a tab for additional application programs, and a patient selector.

* * * * *